| United States Patent [19] | [11] 4,232,032 |
|---|---|
| Boyle et al. | [45] Nov. 4, 1980 |

[54] METHODS, COMPOSITIONS AND CHEMICAL COMPOUNDS FOR USE IN ANIMAL HUSBANDRY

[75] Inventors: Francis T. Boyle; Alan Davies, both of Macclesfield, England

[73] Assignee: Imperial Chemical Industries Limited, London, England

[21] Appl. No.: 669,498

[22] Filed: Mar. 23, 1976

[30] Foreign Application Priority Data

Apr. 8, 1975 [GB] United Kingdom ............... 14316/75

[51] Int. Cl.$^2$ ...................... C07D 319/04; A23K 1/00
[52] U.S. Cl. .................................. 424/269; 260/340.3; 424/278; 424/279; 426/2; 426/807; 548/250
[58] Field of Search ................... 426/2, 807, 623, 624, 426/630, 632, 635, 636; 260/340.3, 308 D, 340.6, 340.7; 119/1; 424/278, 269, 279

[56] References Cited

U.S. PATENT DOCUMENTS

| 2,730,451 | 1/1956 | Aelony | 260/340.3 |
| 2,789,985 | 4/1957 | Harrison | 260/340.3 |

*Primary Examiner*—R. B. Penland
*Attorney, Agent, or Firm*—Cushman, Darby & Cushman

[57] ABSTRACT

The disclosure relates to a method in the practice of animal husbandry which comprises the oral administration to ruminant animals of a benzo[1,3]dioxin derivative. The disclosure also relates to compositions containing such benzo[1,3]dioxin derivatives either in a form suitable for direct feeding to animals, or in the form of a concentrated premix; and to certain of the benzo[1,3]dioxin derivatives used in the method of the invention which are novel compounds.

6 Claims, No Drawings

METHODS, COMPOSITIONS AND CHEMICAL COMPOUNDS FOR USE IN ANIMAL HUSBANDRY

This invention relates to methods, compositions and chemical compounds for use in the husbandry of ruminant animals to improve the rate of growth or feed efficiency, or both.

In ruminant animals, a significant proportion of the gross energy intake in the form of food is lost as methane, formed during fermentation of the food in the rumen, and a further significant proportion of the gross energy intake is lost as heat of fermentation. For example, in lambs, methane can account for about 10% of the gross energy intake, and heat of fermentation accounts for about a further 6% of the gross energy intake. By suppressing methane production in the rumen, thereby also consequentially reducing the energy loss as heat of fermentation, the energy ingested as food is more efficiently utilised, for example by increasing the production of volatile fatty acids, resulting in better rates of growth in the animals, and improved feed efficiency.

Thus, according to the invention, there is provided a method for use in the husbandry of ruminant animals which comprises orally administering to such animals, for example sheep or cattle, a benzo[1,3]dioxin derivative of the formula:

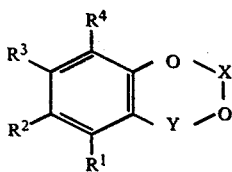

wherein either X is a 2,2,2-trichloroethylidene, 2,2-dichlorovinylidene, or 2,2-dichloro-2-($C_{1-3}$alkoxy)ethylidene radical and Y is a 2,2-dichlorovinylidene or 2,2-dichloroethylidene radical, or X and Y are each a 2,2,2-trichloroethylidene radical; and $R^1$, $R^2$, $R^3$ and $R^4$, which may be the same or different, are each a hydrogen or halogen atom; an amino, carbamoyl, carboxy, chloroformyl, cyano, formyl, formyloxymethyl, hydrazinocarbonyl, hydroxy, nitro, sulphamoyl, sulpho or ammonium sulphonato radical; an alkanoyl, mono- or di-alkanoylamino, alkanoylhydrazonomethyl, alkanoyloxy, alkoxy, alkoxycarbonyl, alkoxyhydroxymethyl, alkyl, mono- or di-alkylsulphamoyl, mono- or di-alkylcarbamoyl, hydrazonoalkyl, hydroxyalkyl or hydroxyalkylcarbamoyl radical, wherein each alkanoyl, alkoxy and alkyl part is of up to 4 carbon atoms and is optionally substituted by one or more halogen atoms, especially chlorine atoms; a benzyl, benzyloxy, benzylideneamino, phenylhydrazinomethyl, mono- or di-phenylsulphamoyl or phenylthioureido radical, in each of which the phenyl ring is optionally substituted by one to three halogen atoms, especially chlorine atoms, or $C_{1-4}$ alkoxy or nitro radicals; or a tetrazol-5-yl radical; or, when $R^1$ is a carboxy radical and $R^2$ is a 1-hydroxyalkyl radical, a γ-lactone thereof; and for those compounds containing a carboxy or sulpho group, base addition salts thereof, for example alkali metal and ammonium salts, and for those compounds containing a basic amino group, acid addition salts thereof, for example hydrochloride, sulphate or nitrate salts.

A particular value for X when it is a 2,2-dichloro-2-($C_{1-3}$alkoxy)ethylidene radical is, for example, a 2,2-dichloro-2-ethoxyethylidene radical.

A suitable value for $R^1$, $R^2$, $R^3$ or $R^4$ when it is a halogen atom is, for example, a chlorine, bromine, iodine or fluorine atom, particularly a chlorine or bromine atom, and especially a chlorine atom.

A suitable value for $R^2$ when it is an alkanoyl, mono- or di-alkanoylamino, alkanoylhydrazonomethyl, alkanoyloxy, alkoxy, alkoxycarbonyl, alkyl, mono- or di-alkylsulphamoyl, mono- or di-alkylcarbamoyl, hydrazonoalkyl, alkoxyhydroxyalkyl, hydroxyalkyl or hydroxyalkylcarbamoyl radical as defined above, is, for example an acetyl, propionyl, butyryl, acetamido, propionamido, butyramido, diacetylamino, 2-acetylhydrazonomethyl, 2-propionylhydrazonomethyl, 2-butyrylhydrazonomethyl, acetoxy, propionyloxy, butyryloxy, methoxy, ethoxy, propoxy, butoxy, methoxycarbonyl, ethoxycarbonyl, propoxycarbonyl, butoxycarbonyl, 2,2,2-trichloroethoxycarbonyl, methyl, ethyl, propyl, butyl, methylsulphamoyl, dimethylsulphamoyl, ethylsulphamoyl, diethylsulphamoyl, methylcarbamoyl, dimethylcarbamoyl, ethylcarbamoyl, diethylcarbamoyl, propylcarbamoyl, dipropylcarbamoyl, hydrazonomethyl, 1-hydrazonoethyl, 1-hydroxy-1-methoxymethyl, 1-ethoxy-1-hydroxymethyl, hydroxymethyl, 1-hydroxyethyl, 2,2,2-trichloro-1-hydroxyethyl, 1-hydroxypropyl or 2,2,2-trichloro-1-hydroxyethylcarbamoyl radical.

A suitable value for $R^2$ when it is a benzoyl, benzoyloxy, benzylideneamino, phenylhydrazonomethyl, mono- or di-phenylsulphamoyl or phenylthioureido radical substituted by one to three halogen atoms or $C_{1-4}$ alkoxy or nitro radicals as defined above, is, for example a 3-chlorobenzoyl, 3,5-dinitrobenzyloxy, 4-chlorobenzylideneamino, 3,4,5-trimethoxybenzylideneamino, 4-nitrobenzylideneamino, 2,4-dinitrophenylhydrazonomethyl, 4-chlorophenylsulphamoyl or 3-methoxyphenylthioureido radical.

A suitable value for $R^3$ is an alkanoyloxy radical as defined above, for example an acetoxy, propionyloxy or butyryloxy radical.

A suitable value for $R^4$ is an alkanoyloxy, alkoxycarbonyl or dialkanoylamino radical as defined above, for example an acetoxy, propionyloxy, butyryloxy, ethoxycarbonyl, 2,2,2-trichloroethoxycarbonyl or diacetylamino radical.

A particular value for $R^1$ is, for example, a hydrogen, chlorine or bromine atom, or a carboxy radical.

A particular value for $R^2$ is, for example, a hydrogen or chlorine atom, or an amino, carbamoyl, carboxy, chloroformyl, cyano, formyl, formyloxymethyl, hydrazinocarbonyl, hydroxy, nitro, sulphamoyl, sulpho, ammonium sulphonato, acetyl, propionyl, acetamido, diacetylamino, propionylhydrazonomethyl, acetoxy, methoxy, methoxycarbonyl, ethoxycarbonyl, n-butoxycarbonyl, methyl, diethylsulphamoyl, diethylcarbamoyl, 1-hydrazonoethyl, 1-hydroxy-1-methoxymethyl, hydroxymethyl, 2,2,2-trichloro-1-hydroxyethyl, 2,2,2-trichloroethoxycarbonyl, 2,2,2-trichloro-1-hydroxyethylcarbamoyl, tetrazol-5-yl, benzoyloxy, benzylideneamino, phenylhydrazonomethyl, phenylthioureido, 4-chlorobenzylideneamino, 3,4,5-trimethoxybenzylideneamino or 4-nitrobenzylideneamino radical.

A particular value for $R^3$ is a hydrogen or bromine atom, or a hydroxy or acetoxy radical.

A particular value for $R^4$ is a hydrogen or chlorine atom, or an acetoxy, amino, carbamoyl, carboxy, 2,2,2- trichloroethoxycarbonyl, diacetylamino, ethoxycarbonyl, hydroxy or nitro radical.

A preferred group of benzo[1,3]dioxin derivatives for use in the method of the invention comprises compounds of the formula I wherein X and Y are each a 2,2,2-trichloroethylidene radical, $R^1$, $R^3$ and $R^4$ are each a hydrogen atom, and $R^2$ is a hydrogen atom or an amino, carboxy, chloroformyl, formyloxymethyl, sulphamoyl or $C_{1-4}$ hydroxyalkyl radical.

A further preferred group of benzo[1,3]dioxin derivatives for use in the method of the invention comprises compounds of the formula I wherein X is a 2,2,2-trichloroethylidene radical, Y is a 2,2-dichlorovinylidene radical, $R^1$, $R^3$ and $R^4$ are each a hydrogen atom, and $R^2$ is an amino, di($C_{1-4}$alkyl)carbamoyl, carboxy, nitro or tetrazol-5-yl radical.

Particular preferred benzo[1,3]dioxin derivatives for use in the method of the invention are 2,4-bis(trichloromethtyl)benzo[1,3]dioxin, 6-amino-2,4-bis(trichloromethyl)benzo[1,3]dioxin, 2,4-bis(trichloromethyl)benzo[1,3]dioxin-6-carboxylic acid, 2,4-bis(trichloromethyl)benzo[1,3]dioxin-6-carbonyl chloride, 6-hydroxymethyl-2,4-bis(trichloromethyl)benzo[1,3]dioxin, 6-sulphamoyl-2,4-bis(trichloromethyl)benzo[1,3]dioxin, 4-dichloromethylene-6-nitro-2-trichloromethylbenzo[1,3]dioxin, 6-amino-4-dichloromethylene-2-trichloromethylbenzo[1,3]dioxin, 4-dichloromethylene-6-diethylcarbamoyl-2-trichloromethylbenzo[1,3]dioxin, 4-dichloromethylene-2-trichloromethylbenzo[1,3]dioxin-6-carboxylic acid, 4-dichloromethylene-6-(tetrazol-5-yl)-2-trichloromethylbenzo[1,3]dioxin, 4-dichloromethyl-2-trichloromethylbenzo[1,3]dioxin-6-carboxylic acid and 6-formyloxymethyl-2,4-bis(trichloromethyl)benzo[1,3]dioxin.

In the method of the invention, the benzo[1,3]dioxin derivative is preferably administered orally to the animals as part of their normal food or drink, that is to say in admixture with an ordinary solid feedstuff or feedblocks, incorporated into a salt lick, or dissolved in the drinking water, or in the form of a slow-release, intraruminal pellet. The benzo[1,3]dioxin derivative is incorporated into food, feed block, salt lick or drinking water to such an extent that each animal ingests from 0.01 mg./kg. body weight to 30 mg./kg. bodyweight per day of the benzo[1,3]dioxin derivative or from 0.01 mg./kg. to 10 mg./kg. per day of a preferred benzo[1,3]dioxin derivative.

According to a further feature of the invention, there is provided a composition for use in the method of the invention which comprises a benzo[1,3]dioxin derivative, as defined above, together with a solid or liquid edible, non-toxic diluent or carrier.

Suitable benzo[1,3]dioxin derivatives for use in the composition of the invention are those defined above, and preferred groups of benzo[1,3]dioxin derivatives and particular preferred individual compounds for use in the composition of the invention are those mentioned above.

A suitable liquid diluent or carrier is, for example, drinking water. A suitable solid, edible, non-toxic diluent or carrier may be, for example, a conventional nutritionally balanced ruminant feedstuff, for example a typical cattle or sheep diet consisting of cereal products, such as barley meal, maize meal or wheat feed, nut and seed products, such as decorticated ground nut cake or cotton seed cake, or extracted cotton seed cake, together with minor amounts of, for example, feather meal, seaweed meal, bone meal, bone flour, chalk, salt, urea, molasses, vitamins and trace minerals; or it may be an inert solid diluent or carrier of no nutritional value, for example kaolin, talc, calcium carbonate, fuller's earth, attapulgus clay, ground oyster shells, ground limestone; or starch or lactose.

The composition of the invention may take the form of a supplemented feedstuff for direct feeding to animals, in which case it will contain from 5 ppm to 3000 ppm of a benzo[1,3]dioxin derivative, or from 5 ppm to 1000 ppm of a preferred benzo[1,3]dioxin derivative in admixture with a conventional ruminant feedstuff; or it may take the form of a concentrated premix for dilution with a conventional ruminant feedstuff to produce a supplemented feedstuff suitable for direct feeding, and such a premix will contain from 0.3% w/w to 50% w/w of a benzo[1,3]dioxin derivative in admixture with either a conventional, nutritionally balanced ruminant feedstuff, an inert solid diluent, for example ground limestone, or starch or lactose.

According to a further feature of the invention there is provided a process for the manufacture of a solid composition of the invention which comprises uniformly mixing a benzo[1,3]dioxin derivative as defined above with a solid, edible, non-toxic diluent or carrier.

The benzo[1,3]dioxin is preferably serially diluted with the diluent or carrier in two or more successive stages, to ensure even mixing. Certain of the benzo[1,3]dioxin derivatives defined above are novel compounds. Thus, according to a further feature of the invention there is provided a novel benzo[1,3]dioxin derivative of the formula I wherein:

(a) X and Y are both 2,2,2-trichloroethylidene radicals, $R^2$ is a hydrogen atom, and $R^1$, $R^3$ and $R^4$, which may be the same or different, have any of the meanings defined above, provided that not all of $R^1$, $R^3$ and $R^4$ are hydrogen atoms; (b) X and Y are both 2,2,2-trichloroethylidene radicals, $R^1$, $R^3$ and $R^4$ are hydrogen atoms, and $R^2$ is a bromine, iodine or fluorine atom; a formyl, formyloxymethyl, hydrazinocarbonyl or hydroxy radical; an alkanoyl, alkanoylhydrazonomethyl, alkanoyloxy, alkoxy, alkoxyhydroxymethyl, mono- or dialkylsulphamoyl, mono- or dialkylcarbamoyl, hydrazonoalkyl or hydroxyalkyl radical, wherein each alkanoyl, alkoxy or alkyl part is of up to 4 carbon atoms, a mono- or dialkanoylamino radical wherein each alkyl part is of 3 or 4 carbon atoms, or an alkyl radical of 3 or 4 carbon atoms, any of which radicals is optionally substituted by halogen atoms, especially chlorine atoms; a chloroalkoxycarbonyl radical of up to 4 carbon atoms; a hydroxyalkylcarbamoyl radical wherein the alkyl part is of 1 to 4 carbon atoms, optionally substituted by halogen atoms, except 2,2,2-trichloro-1-hydroxyethylcarbamoyl; or a benzoyl, benzoyloxy, benzylideneimino, phenylhydrazonomethyl, diphenylsulphamoyl or phenylthioureido radical, in each of which the phenyl ring is substituted by one to three halogen atoms, especially chlorine atoms, or $C_{1-4}$ alkoxy or nitro radicals; or a phenylsulphamoyl radical substituted by one to three halogen atoms, especially chlorine atoms, or $C_{1-4}$ alkoxy, or nitro radicals;

(c) X and Y are both 2,2,2-trichloroethylidene radicals, and $R^1$, $R^2$, $R^3$ and $R^4$ have any of the meanings defined above provided that not more than two are hydrogen atoms, and excepting compounds wherein: $R^2$ is a nitro radical, and either $R^3$ is a methyl radical or $R^4$ is a methyl or nitro radical; $R^2$ is an amino radical, and either $R^3$ is a bromine atom or $R^4$ is an amino or methyl radical; $R^2$ is an acetamido radical and $R^3$ is a bromine atom; $R^2$ is a benzamido radical and $R^4$ is a methyl radical; $R^2$ is a hydroxy or methoxy radical and $R^1$ and $R^3$ are chlorine atoms; $R^2$ is a methyl radical and either $R^3$ is a nitro radical or $R^4$ is a nitro or amino radical; or $R^2$ is a chlorine atom and either $R^4$ is a chlorine atom, or an amino, acetamido or nitro radical, or $R^1$ and $R^4$ are chlorine atoms; or $R^2$ is a 2,2,2-trichloro-1-hydroxyethyl radical and $R^1$ is a carboxy radical, and $R^1$ and $R^2$ together form a γ-lactone ring, and $R^3$ and $R^4$ are both acetoxy radicals; and any of $R^1$, $R^2$, $R^3$ and $R^4$ not otherwise defined are hydrogen atoms;

(d) X and Y are both 2,2-dichlorovinylidene radicals, and $R^1$, $R^2$, $R^3$ and $R^4$ have any of the meanings defined above, excepting those compounds wherein: $R^2$ is an amino radical; $R^1$ and $R^3$ are chlorine atoms and $R^2$ is a hydroxy or methoxy radical; $R^2$ is a methyl radical and either $R^3$ is a nitro radical or $R^4$ is an amino radical; and any of $R^1$, $R^2$, $R^3$ and $R^4$ not otherwise defined are hydrogen atoms;

(e) X is a 2,2,2-trichloroethylidene radical, Y is a 2,2-dichlorovinylidene radical, and $R^1$, $R^2$, $R^3$ and $R^4$ have the meanings defined above, excepting those compounds wherein $R^2$ is a nitro radical and either $R^3$ is a methyl radical or $R^4$ is a nitro radical, and any of $R^1$, $R^3$ and $R^4$ not otherwise defined are hydrogen atoms;

(f) X is a 2,2-dichloro-2-($C_{1-4}$alkoxy)ethylidene radical, for example a 2,2-dichloro-2-ethoxyethylidene radical, Y is a 2,2-dichlorovinylidene radical and $R^1$, $R^2$, $R^3$ and $R^4$ have the meanings defined above;

(g) X is a 2,2,2-trichloroethylidene radical, Y is a 2,2-dichloroethylidene radical and $R^1$, $R^2$, $R^3$ and $R^4$ have the meanings defined above.

Suitable values for $R^1$, $R^2$, $R^3$ are those given above.

Particular values for $R^1$, $R^3$ and $R^4$ in compounds of type (a), (f) and (g) are those given above.

In compounds of type (b), a particular value for $R^2$ is, for example, a formyl, formyloxymethyl, hydroxy, acetyl, propionyl, diacetylamino, propionylhydrazonomethyl, acetoxy, methoxy, methoxycarbonyl, ethoxycarbonyl, n-butoxycarbonyl, methyl, diethylsulphamoyl, 1-hydrazonoethyl, 1-hydroxy-1-methoxymethyl, hydroxymethyl, 2,2,2-trichloroethoxycarbonyl, benzoyloxy, phenylhydrazonomethyl, benzylideneamino, 4-chlorobenzylideneamino, 3,4,5-trimethoxybenzylideneamino or 4-nitrobenzylideneamino radical.

In compounds of type (c), a particular value for $R^2$ is, for example, a carboxy, methyl or diacetylamino radical and a particuar value for $R^4$ is, for example, a carboxy, carbamoyl, diacetylamino, ethoxycarbonyl, 2,2,2-trichloroethoxycarbonyl or nitro radical. Particular compounds of this type are those wherein $R^2$ is a carboxy radical and $R^4$ is a nitro radical, $R^2$ and $R^4$ are both diacetylamino radicals, or $R^2$ is a methyl radical and $R^4$ is a carboxy, carbamoyl, ethoxycarbonyl or 2,2,2-trichloroethoxycarbonyl radical.

In compounds of type (d), a particular value for $R^2$ is, for example an amino, carbamoyl, carboxy or cyano radical.

In compounds of type (e), a particular value for $R^2$ is, for example, an amino, carboxy, cyano, hydrazinocarbonyl, diethylcarbamoyl, sulphamoyl, tetrazol-5-yl radical.

Preferred novel benzo[1,3]dioxin derivatives for use in the method or the composition of the invention are 6-hydroxymethyl-2,4-bis(trichloromethyl)benzo[1,3]dioxin, 6-sulphamoyl-2,4-bis(trichloromethyl)benzo[1,3]dioxin, 4-dichloromethylene-6-diethylcarbamoyl-2-trichloromethylbenzo[1,3]dioxin, 4-dichloromethylene-2-trichloromethylbenzo[1,3]dioxin-6-carboxylic acid, 4-dichloromethylene-6-(tetrazol-5-yl)-2-trichloromethylbenzo[1,3]dioxin, 6-amino-4-dichloromethylene-2-trichloromethylbenzo[1,3]dioxin, 4-dichloromethyl-2-trichloromethylbenzo[1,3]dioxin-6-carboxylic acid, and 6-formyloxymethyl-2,4-bis(trichloromethyl)benzo[1,3]dioxin.

The novel benzo[1,3]dioxin deritives of the invention may be manufactured by methods known in themselves for the manufacture of analogous compounds. Thus, according to a further feature of the invention the following processes are provided for the manufacture of a novel benzo[1,3]dioxin of the formula I, wherein $R^1$, $R^2$, $R^3$, $R^4$, X and Y have the meanings defined above in the definition of new compounds, unless otherwise specified:

(a) the reaction of a phenol of the formula:

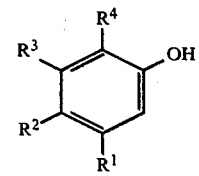

II with two molecular equivalent proportions of chloral hydrate in the presence of a strong acid, for example sulphuric acid, whereafter, when a benzo[1,3]dioxin derivative wherein Y is a 2,2-dichlorovinylidene radical or both X and Y are 2,2-dichlorovinylidene radicals is required, the product so obtained, wherein X and Y are both 2,2,2-trichloroethylidene radicals, is reacted with respectively one or two molecular equivalents of an alkali metal azide or cyanide, or a base, for example an alkali metal hydroxide such as sodium hydroxide, an alkali metal alkanoate such as sodium acetate, or an alkali metal alkoxide such as sodium ethoxide, whereafter if desired particular substituents $R^1$, $R^2$, $R^3$ and $R^4$ may be transformed to other substituents as defined above by conventional methods known in the art of organic chemistry.

Examples of such transformations are the esterification of a carboxylic acid substituent to produce an alkoxycarbonyl substituent; the reduction of an alkoxycarbonyl substituent to a hydroxymethyl substituent; the acetylation of an amino substituent; or the diazotisation and subsequent reduction of an amino substituent to give a hydrogen substituent. Many other examples of conventional transformations of one claimed substituent to another will be readily apparent to a chemist of normal skill;

(b) for those compounds wherein at least one of $R^1$, $R^2$, $R^3$ and $R^4$ is an acylamino or acyloxy radical, the reaction of a corresponding benzo[1,3]dioxin derivative of the formula I, wherein at least one of $R^1$, $R^2$, $R^3$ and $R^4$ is an amino or hydroxy radical, with an alkanoyl or aroyl halide, for example acetyl chloride or benzoyl chloride;

(c) for those compounds wherein at least one of $R^1$, $R^2$, $R^3$ and $R^4$ is a hydrogen atom, the reaction of a corresponding benzo[1,3]dioxin derivative of the formula I, wherein at least one of $R^1$, $R^2$, $R^3$ and $R^4$ is a diazo radical, with an acid, for example concentrated sulphuric acid, and a reducing agent, for example ethanol;

(d) for those compounds wherein at least one of $R^1$, $R^2$, $R^3$ and $R^4$ is a formyl radical, the reduction of a corresponding benzo[1,3]dioxin derivtive of the formula I, wherein at least one of $R^1$, $R^2$, $R^3$ and $R^4$ is a chloroformyl radical, for example with a complex metal hydride such as tri-t-butoxy lithium aluminium hydride;

(e) for those compounds wherein at least one of $R^1$, $R^2$, $R^3$ and $R^4$ is an alkoxyhydroxymethyl radical, the reaction of a corresponding benzo[1,3]dioxin derivative of the formula I, wherein at least one of $R^1$, $R^2$, $R^3$ and $R^4$ is a formyl radical, with an alkanol of 1 to 4 carbon atoms, for example methanol or ethanol, in the presence of an acid;

(f) for those compounds wherein at least one of $R^1$, $R^2$, $R^3$ and $R^4$ is a sulphamoyl radical or a mono- or di-alkylsulphamoyl radical, the reaction of a corresponding benzo[1,3]dioxin derivative of the formula I, wherein at least one of $R^1$, $R^2$, $R^3$ and $R^4$ is a chlorosulphonyl radical, with ammonia or a mono- or di-alkylamine wherein each alkyl part is of 1 to 4 carbon atoms;

(g) for those compounds wherein at least one of $R^1$, $R^2$, $R^3$ and $R^4$ is a benzylideneamino radical, the reaction of a corresponding benzo[1,3]dioxin derivative of the formula I, wherein at least one of $R^1$, $R^2$, $R^3$ and $R^4$ is an amino radical, with a benzaldehyde, optionally substituted by one to three halogen atoms, or $C_{1-4}$ alkoxy or nitro radicals;

(h) for those compounds wherein at least one of $R^1$, $R^2$, $R^3$ and $R^4$ is a phenylthioureido radical, the reaction of a corresponding benzo[1,3]dioxin derivative of the formula I, wherein at least one of $R^1$, $R^2$, $R^3$ and $R^4$ is an amino radical, with a phenylisothiocyanate, optionally substituted by one to three halogen atoms, or $C_{1-4}$ alkoxy or nitro radicals;

(i) for those compounds wherein at least one of $R^1$, $R^2$, $R^3$ and $R^4$ is a bromine atom, the reaction of a corresponding benzo[1,3]dioxin derivative of the formula I, wherein at least one of $R^1$, $R^2$, $R^3$ and $R^4$ is a hydrogen atom, with bromine;

(j) for those compounds wherein at least one of $R^1$, $R^2$, $R^3$ and $R^4$ is an alkoxycarbonyl radical, or a carbamoyl, mono- or di-alkylcarbamoyl radical, the reaction of a corresponding benzo[1,3]dioxin derivative of the formula I, wherein at least one of $R^1$, $R^2$, $R^3$ and $R^4$ is a chloroformyl radical, with respectively a $C_{1-4}$ alkanol optionally substituted by one or more halogen atoms, or ammonia or a mono- or dialkylamine, wherein each alkyl part is of 1 to 4 carbon atoms;

(k) for those compounds wherein at least one of $R^1$, $R^2$, $R^3$ and $R^4$ is a hydroxy radical, the reaction of a corresponding benzo[1,3]dioxin derivative of the formula I, wherein at least one of $R^1$, $R^2$, $R^3$ and $R^4$ is a diazo radical, with an acid, for example concentrated sulphuric acid, in an aqueous medium;

(l) for those compounds wherein at least one of $R^1$, $R^2$, $R^3$ and $R^4$ is a formyloxymethyl radical, the reaction of a corresponding benzo[1,3]dioxin derivative of the formula I, wherein at least one of $R^1$, $R^2$, $R^3$ and $R^4$ is a hydroxymethyl radical, with a $C_{1-4}$ alkyl formate, for example methyl formate, in the presence of an acid;

(m) for those compounds wherein at least one of $R^1$, $R^2$, $R^3$ and $R^4$ is a hydrazinocarbonyl radical, the reaction of a corresponding benzo[1,3]dioxin derivative of the formula I, wherein at least one of $R^1$, $R^2$, $R^3$ and $R^4$ is an alkoxycarbonyl radical, with hydrazine hydrate;

(n) for those compounds wherein X is a 2,2,2-trichloroethylidene radical and Y is a 2,2-dichlorovinylidene radical, the reaction of a corresponding benzo[1,3-]dioxin derivative of the formula I, wherein X and Y are each a 2,2,2-trichloroethylidene radical, with an alkali metal azide or cyanide, for example sodium azide or cyanide, or an alkali metal alkanoate or alkoxide.

(o) for those compounds wherein X and Y are each a 2,2-dichlorovinylidene radical, the reaction of a corresponding benzo[1,3]dioxin derivative of the formula I, wherein X and Y are each a 2,2,2-trichloroethylidene radical, with a strong base, for example an alkali metal alkoxide such as potassium t-butoxide;

(p) for those compounds wherein at least one of $R^1$, $R^2$, $R^3$ and $R^4$ is a cyano radical, the dehydration of a corresponding benzo[1,3]dioxin derivative of the formula I, wherein at least one of $R^1$, $R^2$, $R^3$ and $R^4$ is a carbamoyl radical, for example with thionyl chloride;

(q) for those compounds wherein X is a 2,2,2-trichloroethylidene radical, and Y is a 2,2-dichloroethylidene radical, the reaction of a 2-(2,2-dichloro-1-hydroxyethyl)phenol of the formula:

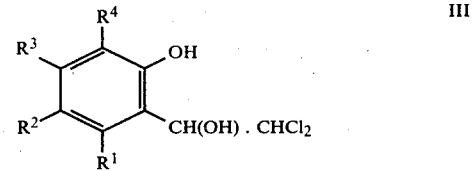

III with chloral hydrate in the presence of a strong acid, for example concentrated sulphuric acid;

(r) for those compounds wherein X is a 2,2-dichloro-2-($C_{1-4}$-alkoxy)ethylidene radical and Y is a 2,2-dichlorovinylidene radical, the reaction of a corresponding benzo[1,3]dioxin derivative of the formula I, wherein X and Y are each a 2,2,2-trichloromethyl radical, with an alkali metal $C_{1-4}$-alkoxide, for example a sodium $C_{1-4}$-alkoxide;

(s) for those compounds wherein at least one of $R^1$, $R^2$, $R^3$ and $R^4$ is an alkanoylhydrazonomethyl, hydrazonoalkyl or phenylhydrazonomethyl radical, the reaction of a corresponding benzo[1,3]dioxin derivative of the formula I, wherein at least one of $R^1$, $R^2$, $R^3$ and $R^4$ is a formyl or alkanoyl radical, with respectively an alkanoylhydrazine wherein the alkanoyl part is of up to 4 carbon atoms, hydrazine, or a phenylhydrazine wherein the phenyl ring is optionally substituted by one to three halogen atoms or $C_{1-4}$ alkoxy or nitro radicals; or (t) for those compounds wherein at least one of $R^1$, $R^2$, $R^3$ and $R^4$ is an alkoxy radical, the reaction of a corresponding benzo[1,3]dioxin derivative of the formula I wherein at least one of $R^1$, $R^2$, $R^3$ and $R^4$ is a hydroxy radical, with a $C_{1-4}$-alkyl halide, for example an alkyl iodide.

In process (n), it will be appreciated that if one or more of $R^1$, $R^2$, $R^3$ and $R^4$ is a cyano radical and an excess of alkali metal azide is used, one or more of the cyano radicals will be converted into one or more tetrazol-5-yl radicals during the course of the reaction.

The starting material of the formula III may be obtained by acid hydrolysis of a corresponding benzo[1,3-]dioxin of the formula I wherein X and Y are each a dichloromethylene radical, to give a 2-dichloroacetylphenol, which is reduced to give the required starting material III.

The invention is illustrated but not limited by the following examples:

EXAMPLE 1

A solution of ethyl 2,4-bis(trichloromethyl)benzo[1,3]dioxin-6-carboxylate (2.0 g.) in anhydrous ether (25 ml.) was added at room temperature during 20 minutes to a suspension of lithium aluminium hydride (0.2 g.) in anhydrous ether (25 ml.). The mixture was stirred for 1 hour, then ethyl acetate (5 ml.) was added, followed by water (10 ml.). The mixture was filtered, and the ether layer of the filtrate was separated. The aqueous phase was extracted with ether (3×10 ml.), the combined extracts were dried, and the solvent was evaporated. The residue was crystallised from ethanol to give 6-hydroxymethyl-2,4-bis(trichloromethyl)benzo[1,3]dioxin, m.p. 134°–136° C.

EXAMPLE 2

A mixture of 2,4-bis(trichloromethyl)benzo[1,3]dioxin-6-carbonyl chloride (5.0 g.) and 2,2,2-trichloroethanol (25 ml.) was warmed on a steam bath for 2 hours. The reaction mixture was cooled, and water was added to produce a white precipitate which was filtered off and crystallised from a mixture of ether and petroleum ether (b.p. 60°–80° C.) to give 2,2,2-trichloroethyl 2,4-bis(trichloromethyl)benzo[1,3]dioxin-6-carboxylate, m.p. 129°–130° C.

In a similar manner, using the appropriate alcohol in place of 2,2,2-trichloroethanol, there were obtained: methyl 2,4-bis(trichloromethyl)benzo[1,3]dioxin-6-carboxylate, m.p. 149.5°–150.5° C.; and n-butyl 2,4-bis(trichloromethyl)benzo[1,3]dioxin-6-carboxylate, m.p. 60°–62° C.

EXAMPLE 3

Nitric acid (d=1.54, 10 ml.) was added to a stirred suspension of 2,4-bis(trichloromethyl)benzo[1,3]dioxin-6-carboxylic acid (5 g.) in concentrated sulphuric acid (25 ml.), and the resulting suspension was stirred at room temperature for 2 hrs. The reaction mixture was filtered, and the solid product was crystallised from a mixture of petroleum ether (b.p. 60°–80° C.) and ether to give 8-nitro-2,4-bis(trichloromethyl)benzo[1,3]dioxin-6-carboxylic acid, m.p. 211°–212° C.

EXAMPLE 4

A mixture of 2,4-bis(trichloromethyl)benzo[1,3]dioxin-6-carbonyl chloride (2 g.) and diethylamine (25 ml.) was heated under reflux for 2 hrs., cooled, and filtered to remove diethylamine hydrochloride. The filtrate was evaporated to dryness under reduced pressure, and the residue was crystallised from ethanol to give 4-dichloromethylene-N,N-diethyl-2-trichloromethylbenzo[1,3]dioxin-6-carboxamide, m.p. 123°–124° C.

EXAMPLE 5

Premixes suitable for dilution with an animal feedstuff may be manufactured by incorporating 10, 25, 50, 100 or 250 g. of 2,4-bis(trichloromethyl)benzo[1,3]dioxin-6-carboxylic acid in ground limestone so that the final weight of the premix is 500 g.

Similar premixes may be manufactured using similar quantities of any other benzo[1,3]dioxin derivative as hereinbefore defined.

EXAMPLE 6

An animal feedstuff suitable for direct feeding to ruminants may be manufactured by intimately mixing 500 g. of a premix, obtained as described in Example 5, with 999.5 kg. of a typical cattle feeding stuff, to obtain a ruminant feedstuff containing 10, 25, 50, 100 or 250 g. of a benzo[1,3]dioxin derivative per metric ton, according to the concentration of benzo[1,3]dioxin derivative in the premix used.

Suitable cattle feedingstuffs are:

| Dairy Cake | cwt. |
| --- | --- |
| Barley meal | 10¼ |
| Maize meal | 1 |
| Decorticated ground nut cake | 1 |
| Decorticated cotton seed cake | 1 |
| Extracted cotton seed cake | 1 |
| Wheat feed | 3 |
| Feather meal | ¼ |
| Seaweed meal | ¼ |
| Bone meal | ¼ |
| Chalk | ¼ |
| Molasses | 1½ |
| Vitamins and trace mineral mix | ¼ |
| | 20 |
| Beef Cube | |
| Barley meal | 11 cwt. |
| Wheat feed | 5¼ cwt. |
| Decorticated ground nut cake | ¼ cwt. |
| Extracted ground nut cake | 42 lbs. |
| Bone flour | ¼ cwt. |
| Chalk | 42 lbs. |
| Salt | 14 lbs |
| Molasses | 2 cwt. |
| Urea | ¼ cwt. |
| Vitamins and trace mineral mix | 14 lbs. |
| | 20 cwt. |

EXAMPLE 7

The ability of the benzo[1,3]dioxin derivatives to inhibit the production of methane without increasing the production of hydrogen, and to increase the production of useful fatty acids, is demonstrated in vivo as follows:

A sheep fitted with a ruminal fistula is starved overnight, and then is offered its normal diet supplemented with 60 mg./kg. of 2,4-bis(trichloromethyl)benzo[1,3-]dioxin-6-carboxylic acid. Samples of rumen fluid (15 to 20 mls.) are then withdrawn through the fistula at hourly intervals. Each sample is filtered, and 1 ml. of 1% w/v sucrose solution is added to 9 ml. of the filtrate in a McCartney bottle, which is then closed with a rubber seal. The bottle is then filled with nitrogen through a hypodermic needle pushed through the rubber seal, and the displaced air is vented through a second similar needle. The bottle is incubated at 39° C. for 3 hours, and the composition of the gas in the bottle above the rumen fluid is sampled, and analysed by gas chromatography.

The following results were obtained:

| Time (hrs.) | Methane % v/v | Hydrogen % v/v | Acetic Acid µg./ml. | Propionic Acid µg./ml. | Butyric Acid µg./ml. |
| --- | --- | --- | --- | --- | --- |
| 1 | 0.2 | 0.2 | 1.93 | 1.74 | 0.53 |
| 2 | 0.3 | 0.1 | 1.89 | 1.77 | 0.59 |
| 3 | 0.2 | 0.3 | 1.91 | 1.80 | 0.60 |
| 4 | 0.2 | 0.0 | 2.01 | 1.87 | 0.64 |
| Control | 0.9 | 0.0 | 1.81 | 1.13 | 0.45 |

EXAMPLE 8

The ability of the benzo[1,3]dioxin derivatives of the invention to inhibit the production of methane from rumen fluid may conveniently be demonstrated by an in vitro assay, as follows:

Rumen fluid is obtained from a cow via a rumen fistula, and strained to remove large particulate matter. Sterile Macartney bottles are used as fermenters, and are made up to contain 8.9 ml. of strained rumen fluid, 1.0 ml. of 1% w/v sucrose solution, and 0.1 ml. of a solution of a compound under test dissolved in dimethylsulphoxide. The bottle is then closed with a rubber seal fitted with two hypodermic needles passing through it, one of which protrudes just through the seal to provide a gas outlet, while the other protrudes into the solution in the bottle to provide a gas inlet. The air is then flushed from the bottle by introducing nitrogen through the inlet needle, and allowing the air/nitrogen mixture to escape from the bottle through the outlet needle. Nitrogen is passed for 30 seconds, then the supply is shut off, and the outlet needle is removed from the rubber seal first, followed by the inlet needle. The contents of the bottle are gently mixed, and the bottle is maintained at 39°–40° C. in a water bath for 3 hours. The needle of an air-tight syringe is introduced through the rubber cap into the gas space above the liquid, the syringe is filled and emptied several times and a sample of the fermentation gas is withdrawn. The fermentation gas is then analysed by gas chromatography on two columns in succession, first a column packed with a mixture of Porapak Q and Diatomite in the ratio 3:2, which separates carbon dioxide from the mixture, and second a column packed with Molecular Sieve 5A, preconditioned by heating to 250° C. for 1½ hours in argon, which separates methane from hydrogen, nitrogen and oxygen. Methane has the longest retention time, and from the area of the methane peak on the chromatogram, by comparison with chromatograms of standard concentrations of methane, the concentration of methane in the fermentation gas is determined. A test compound is examined at various concentrations in the rumen fluid, usually 1, 3, 10, 30 and 100 μg./ml., and the lowest of these concentrations which achieves more than 50% inhibition of methane production is recorded. For the benzo[1,3]dioxin derivatives indicated in the following table, the minimum 50% inhibitory concentrations (M.I.C.) were as shown:

| $R^2$ | M.I.C. (μg./ml.) | $R^2$ | M.I.C. (μg./ml.) |
|---|---|---|---|
| H | 1 | $C_2H_5.CO$ | 10 |
| Cl | 3 | $C_6H_5.NH.SO_2$ | 3 |
| $NH_2$ | 1 | $CH_3O.CH(OH)$ | 3 |
| $CH_3CO.NH$ | 10 | $CH_3CO$ | 3 |
| $(CH_3CO)_2N$ | 3 | $(C_2H_5)_2N.SO_2$ | 10 |
| CN | 3 | $NH_2.N:C(CH_3)$ | 30 |
| $CH_3$ | 30 | $H.CO$ | 3 |
| COOH | 1 | $CH_3(CH_2)_2CO.NH.N:CH$ | 30 |
| $NH_2CO$ | 3 | $CCl_3.CH(OH).NH.CO$ | 10 |
| Cl.CO | 1 | $C_6H_5.CH:N$ | 10 |
| $CH_3(CH_2)_3O.CO$ | 30 | $4\text{-}Cl.C_6H_4.CH:N$ | 10 |
| $C_2H_5O.CO$ | 10 | $3,4,5\text{-}(CH_3O)_3.C_6H_4.CH:N$ | 10 |
| $CH_3O.CO$ | 10 | $4\text{-}NO_2.C_6H_4.CH:N$ | 30 |
| $HO.CH_2$ | 1 | $C_6H_5NH.CS.NH$ | 10 |
| $H.CO.OCH_2$ | 1 | $C_6H_5NH.N:CH$ | 100 |
| $CCl_3CH_2O.CO$ | 10 | HO | 10 |
| $NO_2$ | 3 | $CH_3CO.O$ | 30 |
| $HSO_3$ | 100 | $CH_3O$ | 30 |
| $NH_4^+.SO_3$ | 100 | $C_6H_5CO.O$ | 30 |
| $NH_2SO_2$ | 1 | | |

EXAMPLE 9

The procedure described in Example 8 was repeated, using the benzo[1,3]dioxin derivatives indicated in the following table, and the results obtained were as shown:

| $R^1$ | $R^2$ | $R^3$ | $R^4$ | M.I.C. (μg./ml.) |
|---|---|---|---|---|
| H | $NO_2$ | H | $NO_2$ | 10 |
| H | $NH_2$ | H | $NH_2$ | 10 |
| Br | $NH_2$ | Br | H | 3 |
| H | $CH_3$ | H | $NO_2$ | 30 |
| H | $CH_3$ | H | $NH_2$ | 10 |
| Cl | Cl | H | Cl | 100 |
| H | COOH | H | $NO_2$ | 3 |
| H | $(CH_3CO)_2N$ | H | $(CH_3CO)_2N$ | 3 |
| H | $CH_3$ | H | COOH | 10 |
| H | $CH_3$ | H | $C_2H_5O.CO$ | 10 |
| H | $CH_3$ | H | $NH_2CO$ | 3 |
| H | $CH_3$ | H | $CCl_3CH_2O.CO$ | 30 |

EXAMPLE 10

The procedure described in Example 8 was repeated, using the benzo[1,3]dioxin derivatives indicated in the following table, and the results obtained were as shown:

| $R^2$ | M.I.C. (μg./ml.) | $R^2$ | M.I.C. (μg./ml.) |
|---|---|---|---|
| $NO_2$ | 1 | COOH | 1 |
| $NH_2SO_2$ | 3 | CN | 3 |
| $NH_2NH.CO$ | 3 | 5-tetrazolyl | 1 |
| $(C_2H_5)_2N.CO$ | 1 | $NH_2$ | 1 |

EXAMPLE 11

The procedure described in Example 8 was repeated, using the benzo[1,3]dioxin derivatives indicated in the following table, and the results obtained were as shown:

[Structure: benzo[1,3]dioxin with R² substituent and two CCl₂ groups with O linkages]

| R² | M.I.C. (µg./ml.) | R² | M.I.C. (µg./ml.) |
|---|---|---|---|
| NH₂ | 30 | CN | 100 |
| NH₂·CO | 100 | COOH | 100 |

EXAMPLE 12

The procedure described in Example 8 was repeated, using the following benzo[1,3]dioxin derivatives, to give the results indicated:

4-dichloromethylene-2-(1,1-dichloro-2-oxabutyl)benzo[1,3]dioxin-6-carboxylic acid, M.I.C.=100 µg./ml.

4-dichloromethyl-2-methylbenzo[1,3]dioxin-6-carboxylic acid, M.I.C.=1 µg./ml.

7,8-dihydroxy-5-(1-hydroxyethyl)-2,4-bis(trichloromethyl)benzo[1,3]dioxin-6-carboxylic acid γ-lactone, M.I.C.=10 µg./ml.

7,8-diacetoxy-5-(1-hydroxyethyl)-2,4-bis(trichloromethyl)benzo[1,3]dioxin-6-carboxylic acid γ-lactone, M.I.C.=10 µg./ml.

EXAMPLE 13

A mixture of 6-amino-2,4-bis(trichloromethyl)benzo[1,3]dioxin (1.0 g.), acetyl chloride (1 ml.) and acetic anhydride (25 ml.) was warmed on a steam bath for 5 hours. The reaction mixture was cooled and evaporated to dryness under reduced pressure. Trituration of the oily residue with aqueous ethanol gave a solid product, which was crystallised from ethanol to give 6-diacetylamino-2,4-bis(trichloromethyl)benzo[1,3]dioxin, m.p. 147°–148° C.

EXAMPLE 14

Solid sodium nitrite (1.34 g.) was added in portions to a boiling suspension of 8-amino-6-methyl-2,4-bis(trichloromethyl)benzo[1,3]dioxin (4.7 g.) in a mixture of absolute ethanol (20 ml.), toluene (5 ml.) and concentrated sulphuric acid (1.34 ml.). The mixture was heated under reflux for 3 hours, cooled to ambient temperature and evaporated to dryness under reduced pressure. The oily residue was triturated with petroleum ether (b.p. 60°–80° C.) and filtered, and the solid was crystallised from aqueous ethanol to give 6-methyl-2,4-bis(trichloromethyl)benzo[1,3]dioxin m.p. 134°–135° C.

EXAMPLE 15

Chloral hydrate (36.4 g.) was added in portions to a stirred solution of p-hydroxypropiophenone (15 g.) in concentrated sulphuric acid (100 ml.). After the addition was completed, the mixture was stirred at room temperature for 3 hours and then kept for 5 days. The reaction mixture was poured onto ice, and the resulting solid product was filtered off, dissolved in diethyl ether (200 ml.) and filtered to remove any metachloral and unreacted starting material. The filtrate was dried, and evaporated to dryness under reduced pressure. Trituration of the residue with petroleum ether (b.p. 60°–80° C.) gave a solid product, which was crystallised from aqueous ethanol to give 6-propionyl-2,4-bis(trichloromethyl)benzo[1,3]dioxin, m.p. 96°–97° C.

In a similar manner using p-hydroxyacetophenone in place of p-hydroxypropiophenone, there was obtained 6-acetyl-2,4-bis(trichloromethyl)benzo[1,3]dioxin, m.p. 104°–105° C., and using 2-hydroxy-4-methylbenzoic acid there was obtained 6-methyl-2,4-bis(trichloromethyl)benzo[1,3]dioxin-8-carboxylic acid, m.p. 290°–291° C.

EXAMPLE 16

Chloral hydrate (36.4 g.) was added to a stirred solution of p-hydroxybenzaldehyde (12.2 g.) in concentrated sulphuric acid (100 ml.) and then kept at ambient temperature for 3 weeks. The reaction mixure was poured onto ice, and the solid product was filtered off, washed thoroughly with water (3×100 ml.), and dried. The solid product was extracted with boiling methanol, from which, on cooling, a crude product crystallised. The crude product was suspended in diethyl ether, filtered through silica to remove unchanged starting material, and the filtrate was concentrated to dryness under reduced pressure. Crystallisation of the residue from methanol gave 6-(1-hydroxy-1-methoxymethyl)-2,4-bis(trichloromethyl)benzo[1,3]dioxin, m.p. 123°–125° C.

EXAMPLE 17

Diethylamine (0.8 g.) was added dropwise to a stirred suspension of 2,4-bis(trichloromethyl)benzo[1,3]dioxin-6-sulphonyl chloride (4.7 g.) in absolute ethanol (20 ml.), the mixture was maintained under gentle reflux for 2 hours, and the resulting solution was allowed to cool slowly to give a crystalline product, which was recrystallised from aqueous methanol to give 6-diethylsulphamoyl-2,4-bis(trichloromethyl)benzo[1,3]dioxin, m.p. 125°–126° C.

EXAMPLE 18

A solution of tri-t-butoxy lithium aluminium hydride (prepared from lithium aluminium hydride (1.75 g.) and dry t-butanol (13 ml.) by the method described in Journal of the American Chemical Society, 1958, 80, 5377) in dry bis(2-methoxyethyl)ether (100 ml.) was added dropwise during 1 hour to a stirred solution of 2,4-bis(-trichloromethyl)benzo[1,3]dioxin-6-carbonyl chloride (20 g.) in dry bis(2-methoxyethyl)ether (100 ml.) at −78° C. The internal temperature was maintained at 50° C. by the addition rate, and after the addition was complete, the reaction mixture was allowed to warm to ambient temperature and then was poured onto crushed ice. The resulting precipitate was removed by filtration, and extracted with boiling glacial acetic acid. The extract was diluted with water, 2,4-bis(trichloromethyl)-benzo[1,3]dioxin-6-carboxaldehyde, m.p. 128°–129° C. crystallised out.

EXAMPLE 19

A mixture of 2,4-bis(trichloromethyl)benzo[1,3]dioxin-6-carboxaldehyde (1.0 g.) and phenylhydrazine (0.27 g.) in chloroform (35 ml.) was heated under gentle reflux for 1 hour. The resulting solution was cooled and evaporated to dryness under reduced pressure, and the residue was crystallised from ethanol to give 6-phenyl-hydrazonomethyl-2,4-bis(trichloromethyl)benzo[1,3]dioxin, m.p. 203°–204° C.

In similar manner, using propionyl-hydrazine in place of phenyl-hydrazine there was obtained 2,4-bis(trichloromethyl)benzo[1,3]dioxin-6-carboxaldehyde-n-propionylhydrazone, m.p. 191°–192° C.

EXAMPLE 20

A mixture of 6-amino-2,4-bis(trichloromethyl)benzo[1,3]dioxin (2.0 g.) and benzaldehyde (0.6 g.) in absolute ethanol (25 ml.) was heated under reflux for 5 hours. On cooling the reaction mixture, 6-benzylideneamino-2,4-bis(trichloromethyl)benzo[1,3]dioxin, m.p. 152°–153° C. crystallised out.

In a similar manner, using the appropriate aldehyde in place of benzaldehyde, there were obtained 6-(4-chlorobenzylidineamino)-2,4-bis-trichloromethyl)benzo[1,3]dioxin, m.p. 171°–172° C., 6-(4-nitrobenzylideneamino)-2,4-bis(trichloromethyl)benzo[1,3]dioxin; and m.p. 169°–171° C.; 6-(3,4,5-trimethoxybenzylideneamino)-2,4-bis(trichloromethyl)benzo[1,3]dioxin, m.p. 122°–124° C.

EXAMPLE 21

A mixture of 6-amino-2,4-bis(trichloromethyl)benzo[1,3]dioxin (1.93 g.) and phenylisothiocyanate (0.7 g.) in chloroform (25 ml.) was heated under reflux for 6 hours. The reaction solution was evaporated to dryness, and the residue was crystallised from benzene to give 6-phenylthioureido-2,4-bis(trichloromethyl)benzo[1,3dioxin, m.p. 112°–113° C.

EXAMPLE 22

A solution of bromine (1.59 ml.) in glacial acetic acid (10 ml.) was added in portions to a stirred suspension of 6-amino-2,4-bis(trichloromethyl)benzo[1,3]dioxin (3.86 g.) in glacial acetic acid (10 ml.). The reaction mixture was then heated slowly to boiling, and was heated under reflux for 15 minutes. After cooling, the crystalline product which separated was removed by filtration, washed with acetic acid, and crystallised from ethanol (20 ml.) to give 6-amino-5,7-dibromo-2,4-bis(trichloromethyl)benzo[1,3]dioxin, m.p. 158°–159° C.

EXAMPLE 23

A mixture of 6,8-diamino-2,4-bis(trichloromethyl)-benzo[1,3]dioxin (1 g.), acetic anhydride (25 ml.) and acetyl chloride (2 ml.) was heated on the steam bath for 10 hours. After cooling, the reaction mixture was evaporated to dryness under reduced pressure, and the residue was triturated with aqueous ethanol. The solid product thus obtained was crystallised from ethanol to give 6,8-bis(diacetylamino)-2,4-bis(trichloromethyl)-benzo[1,3]dioxin, m.p. 182°–183° C.

EXAMPLE 24

A mixture of 6-methyl-2,4-bis(trichloromethyl)benzo[1,3-]dioxin-8-carbonyl chloride (2.0 g.) and ethanol (20 ml.) was warmed in the steam bath for 2 hours. The reaction mixture was cooled to produce a white crystalline precipitate, which was filtered off and crystallised from ethanol to give ethyl 6-methyl-2,4-bis(trichloromethyl)benzo[1,3]dioxin-6-carboxylate, m.p. 128°–129° C.

In a similar manner, using 2,2,2-trichloroethanol in place of ethanol, there was obtained 2,2,2-trichloroethyl 6-methyl-2,4-bis(trichloromethyl)benzo[1,3]dioxin-6-carboxylate m.p. 134°–135° C.

EXAMPLE 25

A mixture of 6-methyl-2,4-bis(trichloromethyl)benzo[1,3]dioxin-8-carbonyl chloride (2.0 g.) concentrated ammonia (10 ml.) and ethanol (10 ml.) was heated under reflux for 2 hours. A complete solution was not obtained, but the reaction mixture was cooled and filtered, and the solid product was washed with ethanol and dried, to give 6-methyl-2,4-bis(trichloromethyl)benzo[1,3]dioxin-8-carboxamide, m.p. 281°–283° C.

EXAMPLE 26

A mixture of 2,4-bis(trichloromethyl)benzo[1,3]dioxin-6-diazonium chloride (5 g.) concentrated sulphuric acid (125 ml.) and water (125 ml.) was stirred and heated at 160° C. for 20 minutes. The reaction mixture was cooled to ambient temperature and the product was filtered off, washed with water, and crystallised from cyclohexane, to give 6-hydroxy-2,4-bis(trichloromethyl)benzo[1,3]dioxin, m.p. 167°–169° C.

The diazonium chloride used as starting material in the above process may be prepared as follows:

A solution of sodium nitrite (1.96 g.) in water (30 ml.) was added to a stirred suspension of 6-amino-2,4-bis(trichloromethyl)benzo[1,3]dioxin (10 g.) in a mixture of hydrochloric acid (40 ml.) and water (180 ml.), cooled to 0°–5° C. The suspension was stirred for 1 hour at 0°–5° C., the mixture was filtered, and the solid product was washed with water, dried and crystallised from water to give 2,4-bis(trichloromethyl)benzo[1,3]dioxin-6-diazonium chloride, m.p. 140°–142° C.

EXAMPLE 27

A mixture of 6-hydroxy-2,4-bis(trichloromethyl)benzo[1,3]dioxin (1.0 g.) and acetic anhydride (10 ml.) was warmed on the steam bath for 15 minutes, and then cooled to ambient temperature. Water (40 ml.) was added, and the mixture stirred for 1 hour. The product was removed by filtration, washed with water, dried and crystallised from ethanol to give 6-acetoxy-2,4-bis(-trichloromethyl)benzo[1,3]dioxin, m.p. 142°–144° C.

EXAMPLE 28

A mixture of 6-hydroxy-2,4-bis(trichloromethyl)benzo[1,3]dioxin (1.0 g.), benzoyl chloride (0.35 ml.) and toluene (20 ml.) was warmed on the steam bath for 1 hour. The resulting solution was cooled to ambient temperature and evaporated to dryness under reduced pressure to give an oily residue. The residue was triturated with ethanol (5 ml.) to give a white solid, which was crystallised from ethanol to give 6-benzoyloxy-2,4-bis(trichloromethylbenzo[1,3]dioxin, m.p. 167°–169° C.

EXAMPLE 29

A solution of 2,4-bis(trichloromethyl)benzo[1,3]dioxin-6-carboxaldehyde (1.0 g.) in diethylether (10 ml.) was added to a mixture of aluminium chloride (1.17 g.) and lithium aluminium hydride (0.95 g.) in diethyl ether (15 ml.). A vigorous reaction was observed during this addition, the mixture was stirred for 1½ hours, and then a solution of methyl formate (5 ml.) in diethyl ether (20 ml.) was added at 0° C. The reaction mixture was allowed to reach ambient temperature, and 20% sulphuric acid (25 ml.) was added. The organic layer was separated, dried, and concentrated under reduced pressure to give an oily product which readily solidified on trituration with petroleum ether (b.p. 60°-80° C.) to give 6-formyloxymethyl-2,4-bis(trichloromethyl)benzo[1,3]dioxin, m.p. 75°-77° C.

EXAMPLE 30

A mixture of 7,8-dihydroxy-6-(2,2,2-trichloro-1-hydroxyethyl)-2,4-bis(trichloromethyl)benzo[1,3]dioxin-5-carboxylic acid γ-lactone (1.0 g.), concentrated sulphuric acid (0.5 ml.) and acetic anhydride (25 ml.) was warmed on a steam bath for 5 hours. The reaction mixture was cooled, and evaporated to dryness under reduced pressure, and the residue was triturated with petroleum ether (b.p. 60°-80° C.) to give a solid product. The solid product was crystallised from ethanol to give 7,8-diacetoxy-6-(2,2,2-trichloro-1-hydroxyethyl)-2,4-bis(trichloromethyl)benzo[1,3]dioxin-5-carboxylic acid γ-lactone, m.p. 209°-210° C.

EXAMPLE 31

A mixture of ethyl 2,4-bis(trichloromethyl)benzo[1,3]dioxin-6-carboxylate (6.4 g.), 100% hydrazine hydrate (3 ml.) and ethanol (30 ml.) was warmed on the steam bath for 30 hours. The reaction mixture was cooled, and then evaporated to dryness under reduced pressure. The oily residue was triturated with petroleum ether (b.p. 60°-80° C.) and the solid product thus obtained was crystallised from ethanol, to give 4-dichloromethylene-2-trichloromethylbenzo[1,3]dioxin-6-carbohydrazide, m.p. 182°-183° C.

EXAMPLE 32

A mixture of 2,4-bis(trichloromethyl)benzo[1,3]dioxin-6-carboxylic acid (2.08 g.), ammonium chloride (0.33 g.) and sodium azide (0.36 g.) in anhydrous dimethylsulphoxide (10 ml.) was warmed on the steam bath for 16 hours. The reaction mixture was cooled, poured onto ice and kept for 16 hours. The white product was filtered off, washed with water and dried, and crystallised from aqueous ethanol to give 4-dichloromethylene-2-trichloromethybenzo[1,3]dioxin-6-carboxylic acid, m.p. 222°-223° C.

In a similar manner, using the appropriate 2,4-bis(trichloromethyl)benzo[1,3]dioxin, there were obtained 6-cyano-4-dichloromethylene-2-trichloromethylbenzo[1,3]dioxin, m.p. 131°-133° C.; and 6-amino-4-dichloromethylene-2-trichloromethylbenzo[1,3]dioxin, m.p. 125°-126° C.

EXAMPLE 33

A mixture of 6-cyano-2,4-bis(trichloromethyl)benzo[1,3]dioxin (1.98 g.), ammonium chloride (0.33 g.) and sodium azide in anhydrous dimethylformamide was warmed on the steam bath for 16 hours. The reaction mixture was cooled, poured onto ice and kept for 16 hours. The amorphous white product was filtered off, triturated with acetic acid, and crystallised from chloroform to give 4-dichloromethylene-6-(tetrazol-5-yl)-2-trichloromethylbenzo[1,3]dioxin, m.p. 222° C.

EXAMPLE 34

A mixture of 2,4-bis(trichloromethyl)benzo[1,3]dioxin-6-carboxamide (3.14 g.) and potassium t-butoxide (2.5 g.) in 50% aqueous dimethylsulphoxide (50 ml.) was heated at 80°-90° C. for 2 hours. The solid product was filtered off, dried and crystallised from ethanol to give 2,4-bis(dichloromethylene)benzo[1,3]dioxin-6-carboxamide, m.p. 217°-218° C.

In a similar manner, using 2,4-bis(trichloromethyl)benzo[1,3]dioxin-6-carboxylic acid, there was obtained 2,4-bis(dichloromethylene)benzo[1,3]dioxin-6-carboxylic acid m.p. 199°-200° C.

EXAMPLE 35

2,4-Bis(dichloromethylene)benzo[1,3]dioxin-6-carboxamide (3.0 g.) was added in portions to a stirred mixture of thionyl chloride (15 ml.) in dimethylformamide (60 ml.) at 50° C. A precipitate rapidly formed which, after cooling the reaction mixture to ambient temperature, was filtered off, dried, and crystallised from ethanol to give 6-cyano-2,4-bis(dichloromethylene)benzo[1,3]dioxin, m.p. 167°-168° C.

EXAMPLE 36

A mixture of 2,2-dichloro-1-(2-hydroxy-5-carboxyphenyl)ethanol (1.25 g.), chloral hydrate (1.0 g.) and concentrated sulphuric acid (12.5 ml.) was stirred at room temperature for 3 days. The reaction mixture was poured onto ice, and the product was filtered off, washed with water, dried and crystallised from aqueous acetic acid to give 4-dichloromethyl-2-trichloromethylbenzo[1,3]dioxin-6-carboxylic acid, m.p. 209° C.

The 2,2-dichloro-1-(2-hydroxy-5-carboxyphenyl)ethanol used as starting material in the above process may be prepared as follows:

A mixture of 2,4-bis(dichloromethylene)benzo[1,3]dioxin-6carboxamide (10 g.), acetic acid (150 ml.) and hydrochloric acid (150 ml.) was heated under reflux for 3 hours. The solution was cooled, and evaporated to dryness under reduced pressure and the residue was crystallised from acidified water to give 4-carboxy-α,α-dichloro-2-hydroxy-acetophenone, m.p. 161°-162° C.

4-Carboxy-α,α-dichloro-2-hydroxyacetophenone (2.49 g.) was added in portions to an ice-cooled solution of sodium borohydride (0.56 g.) in ethanol (10 ml.). The reaction was stirred for 1 hour, and evaporated to dryness to give a yellow oily solid, which on treatment with 2 N hydrochloric acid gave a white solid, which readily crystallised from water to give 2,2-dichloro-1-(2-hydroxy-5-carboxyphenyl)ethanol, m.p. 214°-215° C.

EXAMPLE 37

A mixture of 2,4-bis(trichloromethyl)benzo[1,3]dioxin-6-sulphonamide (2.0 g.), sodium cyanide (1.0 g.), ethanol (25 ml.) and water (10 ml.) was stirred and heated at 55°-60° C. for 24 hours. The reaction mixture was cooled and acidified with concentrated hydrochloric acid. The solid product was filtered off and crystallised from aqueous methanol to give 4-dichloromethylene-2-trichloromethylbenzo[1,3]dioxin-6-sulphonomide, m.p. 151°-152° C.

EXAMPLE 38

A mixture of 6-acetyl-2,4-bis(trichloromethylbenzo[1,3]dioxin (2.0 g.) and 100% hydrazine hydrate (0.25 g.) in absolute ethanol (25 ml.) was heated under reflux for 16 hours, and cooled to give 6-acetyl-2,4-bis(trichloromethyl)benzo[1,3]dioxin hydrazone, m.p. 159° C.

EXAMPLE 39

A solution of sodium hydroxide (0.52 g.) in ethanol (50 ml.) was added dropwise to a stirred solution of 6-hydroxy-2,4-bis(trichloromethyl)benzo[1,3]dioxin (5 g.) in ethanol (100 ml.) and the resulting solution was stirred for 15 minutes. Methyl iodide (1.7 ml.) was then added, the reaction mixture was warmed on a steam bath for 1 hour, and evaporated to dryness under reduced pressure, and the oily residue was triturated with diethyl ether and filtered to remove sodium iodide. The filtrate was chromatographed on silica (Kieselgel 60; 200 g.) and the product was crystallised from ethanol to give 6-methoxy-2,4-bis(trichloromethyl)benzo[1,3]dioxin, m.p. 105°–107° C.

EXAMPLE 40

A mixture of 2,4-bis(trichloromethyl)benzo[1,3]dioxin (20 g.), potassium hydroxide (48 g.) and ethanol (200 ml.) was warmed on the steam bath for 30 minutes during which a white solid formed. Water (200 ml.) was added, giving a red solution which was concentrated to 200 ml. total volume to give a solid sodium salt which was removed by filtration and treated with 2 N hydrochloric acid to liberate the free acid. The white solid proced was extracted with diethyl ether, and the organic extract was dried and concentrated under reduced pressure. The residue was crystallised from cyclohexane to give 2-(1,1-dichloro-1-ethoxymethyl)-4-dichloromethylenebenzo[1,3]dioxin-6-carboxylic acid, m.p. 121°–122° C.

What we claim is:

1. In the practice of ruminant animal husbandry, the method of suppressing methane production in the rumen and thereby improving the rate of growth or feed efficiency or both which comprises orally administering to animals from 0.01 mg/kg body weight to 30 mg/kg body weight per day per animal of a material selected from the group consisting of:

(a) benzo[1,3]dioxin derivatives of the formula:

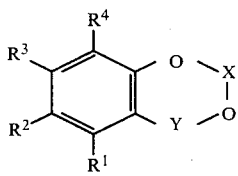

wherein:
X is 2,2,2-trichloroethylidene, 2,2-dichlorovinylidene or 2,2-dichloro-2-($C_{1-3}$ alkoxy)ethylidene;
Y is 2,2-dichlorovinylidene or 2,2-dichloroethylidene;
$R^1$, $R^2$, $R^3$ and $R^4$, which may be the same or different, are: hydrogen, halogen, amino, carbamoyl, carboxy, chloroformyl, cyano, formyl, formyloxymethyl, hydrazinocarbonyl, hydroxy, nitro, sulfamoyl, sulfo, and ammonium sulfonato; alkanoyl, mono-or di-alkanoylamino, alkanoylhydrazonomethyl, alkanoyloxy, alkoxy, alkoxycarbonyl, alkoxyhydroxymethyl, alkyl, mono- and di-alkylsulfamoyl, mono- and di-alkylcarbamoyl, hydrazonoalkyl, hydroxyalkyl and hydroxyalkylcarbamoyl, wherein each alkanoyl, alkoxy and alkyl part is of up to 4 carbon atoms, and is unsubstituted or substituted by one or more halogen atoms; benzoyl, benzoyloxy, benzylideneamino, phenylhydrazonomethyl, mono- and di-phenylsulfamoyl, and phenylthioureido, in each of which the phenyl ring is unsubstituted, or is substituted by one to three halogen, nitro or $C_{1-4}$-alkoxy substituents; or tetrazol-5-yl;

(b) the γ-lactones of benzo[1,3]dioxin derivatives, as defined above, wherein $R^1$ is carboxy and $R^2$ is 1-hydroxyalkyl, unsubstituted or substituted by halogen as defined above;

(c) the base addition salts of benzo[1,3]dioxin derivatives, as defined above, which contain carboxy, or sulfonic acid; and (d) the acid addition salts of benzo[1,3]dioxin derivatives as defined above, which contain amino, and continuing said administration for as long as improved growth rate or feed efficiency through reduced methane production in the rumen is desired, the amount of said material administered being sufficient to reduce the production of methane in the rumen.

2. The method of claim 1 which comprises the oral administration of a material selected from:

(a) benzo[1,3]dioxin derivatives of the formula I wherein:
X is 2,2,2-trichloroethylidene, 2,2-dichlorovinylidene or 2,2-dichloro-2-ethoxyethylidene; or
Y is 2,2-dichlorovinylidene or 2,2-dichloroethylidene;
$R^1$ is hydrogen, chlorine, bromine or carboxy;
$R^2$ is hydrogen, chlorine, amino, carbamoyl, carboxy, chloroformyl, cyano, formyl, formyloxymethyl, hydrazinocarbony hydroxy, nitro, sulfamoyl, sulfo, ammonium sulfonato, acetyl, propionyl, acetamido, diacetylamino, propionylhydrazonomethyl, acetoxy, methoxy, methoxycarbonyl, ethoxycarbonyl, n-butoxycarbonyl, methyl, diethylsulfamoyl, diethylcarbamoyl, 1-hydrazonoethyl, 1-hydroxy-1-methoxymethyl, hydroxymethyl, 2,2,2-trichloroethoxycarbonyl, 2,2,2-trichloro-1-hydroxyethylcarbamoyl, tetrazol-5-yl, benzoyloxy, benzylideneamino, phenylhydrazonomethyl, phenylthioureido, 4-chlorobenzylideneamino, 3,4,5-trimethoxybenzylideneamino or 4-nitrobenzylideneamino;
$R^3$ is hydrogen, bromine, or acetoxy; and
$R^4$ is hydrogen, bromine, acetoxy, amino, carbamoyl, carboxy, 2,2,2-trichloroethoxycarbonyl, diacetylamino, ethoxycarbonyl, hydroxy or nitro;

(b) the γ-lactone of the benzo[1,3]dioxin derivative wherein:
X and Y have the meanings stated in (a) above;
$R^1$ is carboxy;
$R^2$ is 2,2,2-trichloro-1-hydroxyethyl;
$R^3$ and $R^4$ are acetoxy;

(c) the alkali metal and ammonium salts of benzo[1,3-]dioxin derivatives defined in (a) above which contain carboxy or sulfo; and (d) the hydrochlorides, sulphates and nitrates of benzo[1,3]dioxin derivatives defined in (a) above which contain amino.

3. In the practice of ruminant animal husbandry, the method which comprises orally administering to said animals from 0.01 mg/kg body weight to 30 mg/kg body weight per day per animal, a benzo[1,3]dioxin derivative of the formula [I]

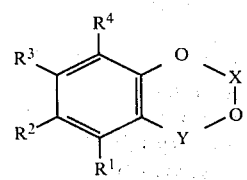

wherein:
X is 2,2,2-trichloroethylidene;
Y is 2,2-dichlorovinylidene;
$R^1$, $R^3$ and $R^4$ are hydrogen;
$R^2$ is amino, di($C_{1-4}$ alkyl)carbamoyl, carboxy, nitro or tetrazol-5-yl, the amount of material administered being sufficient to reduce the production of methane in the rumen.

4. In the practice of ruminant animal husbandry, the method of suppressing methane production in the rumen and thereby improving the rate of growth or feed efficiency or both which comprises orally administering to animals from 0.01 mg/kg body weight to 30 mg/kg body weight per day per animal of a compound selected from the group consisting of 2,4-bis(trichloromethyl)-benzo[1,3]dioxin-6-carboxylic acid, 2,4-bis(trichloromethyl)-benzo[1,3]dioxin-6-carbonyl chloride, 6-hydroxymethyl-2,4-bis(trichloromethyl)benzo[1,3]dioxin, 6-sulphamoyl-2,4-bis(trichloromethyl)-benzo[1,3]dioxin, 4-dichloromethylene-6-nitro-2-trichloromethylbenzo [1,3]dioxin, 6-amino-4-dichloromethylene-2-trichloromethylbenzo [1,3]dioxin, 4-dichloromethylene-6-diethylcarbamoyl-2-trichloromethylbenzo[1,3]dioxin, 4-dichloromethylene-2-trichloromethylbenzo[1,3]dioxin-6-carboxylic acid, 4-dichloromethylene-6-(tetrazol-5-yl)-2-trichloromethylbenzo[1,3]dioxin, 4-dichloromethyl-2-trichloromethylbenzo[1,3]dioxin-6-carboxylic acid, or 6-formyloxymethyl-2,4-bis(trichloromethyl)benzo[1,3]dioxin and continuing said administration for as long as improved growth rate or feed efficiency through reduced methane production in the rumen is desired.

5. A benzo[1,3]dioxin derivative of the formula:

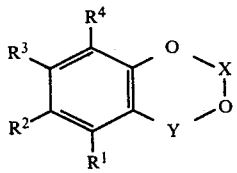

wherein:
(a)
X and Y are both 2,2,2-trichloroethylidene;
$R^2$ is formyl, formyloxymethyl, hydroxy, acetyl, propionyl, diacetylamino, propionylhydrazonomethyl, acetoxy, methoxy, methoxycarbonyl, ethoxycarbonyl, n-butoxycarbonyl, methyl, diethylsulfamoyl, 1-hydroazonoethyl, 1-hydroxy-1-methoxymethyl, hydroxymethyl, 2,2,2-trichloroethoxycarbonyl, benzoyloxy, phenylhydrazonomethyl, benzylideneamino, 4-chlorobenzylideneamino, 3,4,5-trimethoxybenzylideneamino or 4-nitrobenzylideneamino; and
$R^1$, $R^3$ and $R^4$ are hydrogen;
(b)
X and Y are both 2,2,2-trichloroethylidene;
$R^1$ and $R^3$ are hydrogen;
$R^2$ is carboxy, methyl or diacetylamino; and
$R^4$ is carboxy, carbamoyl, diacetylamino, ethoxycarbonyl, 2,2,2-trichloroethoxycarbonyl or nitro;
(c)
X and Y are both 2,2-dichlorovinylidene;
$R^1$, $R^3$ and $R^4$ are hydrogen; and
$R^2$ is amino, carbamoyl, carboxy or cyano; and
(d)
X is 2,2,2-trichloroethylidene;
Y is 2,2-dichlorovinylidene;
$R^1$, $R^3$ and $R^4$ are hydrogen; and
$R^2$ is amino, carboxy, cyano, hydrazinocarbonyl, diethylcarbamoyl, sulfamoyl or tetrazol-5-yl.

6. The benzo[1,3]dioxin derivatives 6-hydroxymethyl-2,4-bis(trichloromethyl)benzo[1,3]dioxin, 4-dichloromethylene-6-diethylcarbamoyl-2-trichloromethylbenzo[1,3]dioxin, 4-dichloromethylene-2-trichloromethylbenzo[1,3]dioxin-6-carboxylic acid, 4-dichloromethylene-6-(tetrazol-5-yl)-2-trichloromethylbenzo[1,3]dioxin, 6-amino-4-dichloromethylene-2-trichloromethylbenzo[1,3]dioxin, 4-dichloromethyl-2-trichloromethylbenzo[1,3]dioxin-6-carboxylic acid or 6-formyloxymethyl-2,4-bis(trichloromethyl)benzo[1,3]dioxin.

* * * * *